United States Patent [19]

Rosenberg

[11] Patent Number: 4,894,440

[45] Date of Patent: Jan. 16, 1990

[54] METHOD OF ISOLATING MEGAKARYOCYTE STIMULATORY FACTOR

[75] Inventor: Robert D. Rosenberg, Brookine, Mass.

[73] Assignee: Massachusetts Institute of Technology, Cambridge, Mass.

[21] Appl. No.: 908,183

[22] Filed: Sep. 17, 1986

[51] Int. Cl.$^4$ ............................................. C07K 3/28
[52] U.S. Cl. .................................. 530/351; 530/350; 530/399; 530/412; 530/413; 530/414; 530/415; 530/418; 530/417; 530/420; 530/830; 530/835; 435/70.3
[58] Field of Search ........ 530/351, 350, 399, 412–415, 530/418–420, 830, 835; 435/68

[56] References Cited

U.S. PATENT DOCUMENTS 4,289,690 9/1981 Pistka et al. ....................... 530/351

OTHER PUBLICATIONS

Bozill et al., *Biochem. J.* 210, 1983, pp. 747–759.
In Vitro Cloning of Normal and Leukemic Cells, ed, Metcalf, Springer–Verlag, N.Y., 1977, pp. 9, 46 and 200.
Jenkins et al, *Blood* 67(3) 1986, pp. 682–688.
Nicola et al., *JBC* 82, 1985, pp. 1526–1530.
Wilbe et al, *PNAS* 82, 1985, pp. 1526–1530.
Emerson et al., *J. Chem. Invest.* 6, 1985, pp. 1286–1290.
T. P. McDonald et al., *Exp. Hematol. 9, 288–296 (1981)*.
J. Levin, et al, *Blood*, 54:166a (abstr.) (1979).
T. P. McDonald, *Biochem. Med.* 21, 146–155 (1979).
P. Cohen et al., *J. Clin. Invest.* 44, 1036 (abstr.) (1965).
E. R. Stanley, *Proc. Natl. Acad. Sci.* USA 82, 2764–2768 (1985).
T. P. McDonald, *J. Lab. Clin. Med.* 85, 59–66 (1975).
S. M. Greenberg, et al. *J. of Biol. Chem.*, 262:3269–3277 (1987).

*Primary Examiner*—Garnette D. Draper
*Attorney, Agent, or Firm*—Hamilton, Brook, Smith & Reynolds

[57] ABSTRACT

A megakarytocyte stimulatory factor (MSF), purified to homogeneity, is an acidic protein (pI=5.1) with an Mr=15,000 which stimulates PF4-like protein synthesis in rat promegakaryoblast cells by as much as 7-fold, and exhibits half-maximal activity at a concentration of 0.8 pM. MSF exhibits no biologic activity corresponding to other known hemopoietic growth factors, and appears to be specific for the megakaryocyte lineage.

In the given examples, MSF was purified to homogeneity (as judged by SDS-PAGE and isoelectric focusing in the presence of 9.2 M urea) from serum-free conditioned medium obtained from cultured human embryonic kidney (HEK) cells, and to near homogeneity from thrombocytopenic plasma. The MSF is isolated by precipitating the MSF with ammonium sulfate at 80% saturation, removing insoluble, non-MSF material and applying the soluble protein to a WGA-Sepharose column, eluting the MSF protein with chitin oligosaccharides, applying the concentrated eluant containing MSF activity to a Biogel P200 column, and chromatographing the eluted MSF fractions on a TSK-G3000 HPLC size exclusion column.

13 Claims, No Drawings

METHOD OF ISOLATING MEGAKARYOCYTE STIMULATORY FACTOR

BACKGROUND OF THE INVENTION

This invention is generally in the field of blood and specifically in the area of platelet proteins.

Blood platelets are the terminal differentiation product of megakaryocytes. Megakaryocytes are believed to originate from the primordial pluripotential stem cells of the bone marrow. The earliest recognizable form is the megakaryoblast which possesses an immature nucleus embedded in basophilic cytoplasm with a minimal number of granules. The complex maturation process involves the formation of a multilobulated, polyploid nucleus and distinctive, highly specialized cytoplasmic granules. Platelets are shed from mature megakaryocytes by a process that is poorly understood.

Although progress has been made in identifying the synthesis of platelet-specific proteins and subcellular structure in maturing megakaryocytes, relatively little is known about the regulation of megakaryocytopoiesis.

Several humoral factors have been postulated to control the ploidization and cytoplasmic maturation of megakaryocytes. These substances have been obtained in crude form and are termed thrombopoietin (TPO) or thrombopoietic stimulatory activity (TSF), depending upon the source from which the activity is derived. The assays used to quantitate the biological activity of these factors are dependent upon measurements of the incorporation of radioisotopes, especially [$^{75}$Se]selenomethionine and $^{35}SO_4$, into the proteins and glycosaminoglycans of newly-formed platelets, all of which are synthesized by the megakaryocytes. Accordingly, these measurements probably reflect the rates of cytoplasmic maturation of megakaryocytes including the development of the specialized cytoplasmic structures integral to platelet function.

Recent data indicates that a megakaryocyte-colony stimulating factor (Meg-CSF) causes the tremendous increase in DNA replications. The second phase, the maturation of the committed precursor cells to fully differentiated megakaryocytes, is thought to be regulated by a humoral factor(s) whose blood concentration is somehow altered by changes in the level of circulating platelets.

This factor(s) increases the transcription rate of proteins for inclusion into multiple secretory granules. The cytoplasm of the mature megakaryocyte contains multiple platelet secretory granules, including alpha-granules, dense granules, and platelet lysosomes. In particular, the alpha-granules are known to contain platelet-derived growth factor (PDGF), beta-thromboglobulin, platelet factor 4 (PF4), and the chondroitin sulfate proteoglycan carrier.

Previous investigators have described procedures for isolating a partially purified thrombopoietically active substance(s), including T. P. McDonald et al. in *Exp. Hematol.* 9, 288–296 (1981), J. Levin et al. in *Blood* 54, 166a (abst.) (1979), and T. P. McDonald in *Biochem. Med.* 21, 146–155 (1979). These partially purified preparations, approximately 100 fold purified, were generally prepared by ammonium sulfate precipitation and chromatography on a lectin column. Although they were shown to have some role in stimulating protein synthesis, no single factor in pure form has been isolated for characterization and application.

It is therefore an object of the present invention to identify and isolate a factor regulating maturation of committed megakaryocyte progenitor cells to fully differentiated megakaryocytes, particularly a factor enhancing the rate of protein synthesis.

It is a further object of the present invention to provide a method for isolation of very pure megakaryocyte stimulatory factor.

It is still a further object of the invention to provide methods for specifically assaying for megakaryocyte stimulatory factor.

It is another object of the present invention to provide nucleotide sequences encoding megakaryocyte stimulatory factor proteins.

SUMMARY OF THE INVENTION

A megakaryocyte stimulatory factor (MSF) which is purified to homogeneity and assayed by its ability to enhance the rate of synthesis of platelet factor 4-like proteins in a rat promegakaryoblast cell line (RPM) and in a megakaryocyte enriched fraction derived from rat bone marrow (Meg-D).

In the given example, MSF is purified to homogeneity ($7.5 \times 10^5$-fold) from serum-free conditioned medium obtained from cultured human embryonic kidney (HEK) cells, and to near homogeneity ($1.44 \times 10^7$-fold) from thrombocytopenic plasma. In the first example, the MSF is isolated by preparing a serum-free HEK cell lysate, centrifuging and concentrating the lysate, precipitating the MSF with ammonium sulfate at 80% saturation, dialyzing into a physiological Tris buffer to remove insoluble, non-MSF material, applying the soluble protein to a WGA-Sepharose column, eluting the MSF protein with chitin oligosaccharides, preferably N-acetylglucosamine trimers, applying the concentrated eluant containing MSF activity to a Biogel P200 column, eluting and concentrating the fractions containing MSF activity using a high ionic strength buffer, chromatographing those fractions on a TSK-G3000 HPLC size exclusion column and eluting the MSF with a low ionic strength buffer. In the second example, a similar purification procedure, with the omission of the Biogel P200 column, is used to isolate MSF from thrombocytopenic plasma.

The $^{125}$I-labeled MSF prepared from HEK cell conditioned medium is homogeneous as judged by SDS-PAGE and isoelectric focusing in the presence of 9.2M urea. MSF is an acidic protein (pI=5.1) with an MR=15,000 which stimulates PF4-like protein synthesis in rat promegakaryoblast cells by as much as 7-fold, and exhibits half-maximal activity at a concentration of 0.8 pM. Approximately three-fold stimulation of protein synthesis by MSF was demonstrated using normal megakaryocytes (Meg-D). MSF exhibits no biologic activity corresponding to other known hemopoietic growth factors, and appears to be specific for the megakaryocyte lineage.

Nucleotide sequences encoding the megakaryocyte stimulatory factor protein are isolated by methods known to those skilled in the art. In the preferred method, RNA is isolated from cells producing megakaryocyte stimulatory factor, cDNA is synthesized from the RNA, the cDNA is inserted into an inducible phage which is then packaged and introduced into an appropriate *E. coli* host, the phage is induced and the cells screened for MSF protein, and the DNA from the cells producing MSF protein isolated and characterized. The gene and cDNA sequences encoding all or part of the MSF are useful in the production of MSF and portions of MSF which can be used as antigens for antibody production or as specific drug targets. The gene or nucleotide sequences can also be modified to produce MSF with enhanced or altered activity.

The purified protein has a number of potential applications, for example, to potentiate platelet function in patients with thrombocytopenia or atherosclerosis, in wound healing, in patients with antibody to platelets, or to make drugs to enhance, alter or decrease platelet function.

DETAILED DESCRIPTION OF THE INVENTION

The present invention is a megakaryocyte stimulatory factor (MSF) purified to apparent homogeneity. In the first example, the MSF is obtained from human embryonic kidney cells using a purification scheme involving ammonium sulfate fractionation, WGA-Sepharose affinity chromatography, Biogel P200 gel filtration, and TSK G3000 HPLC chromatography. The $^{125}$I-labeled MSF has a $M_r=15,000$ as judged by SDS-PAGE, but migrates as a protein of $M_r=9,000$ on analytical size exclusion HPLC, which is consistent with extensive glycosylation. It is necessary to $^{125}$I-label the purified MSF since the factor cannot be visualized with silver staining. The lack of silver staining has been observed for other glycoproteins. The MSF, when examined by isoelectric focusing in the presence of 9.2M urea, exhibits a narrow band at pH 5.1 (bandwidth less than 0.1 pH units). Purified MSF has a strong tendency under non-denaturing conditions to self-associate. Although purified MSF is consistently recovered as a protein of $M_r=9,000$ under the appropriate conditions on gel filtration HPLC, 16% of $^{125}$I-labeled MSF migrates as a high-molecular weight component when rechromatographed under these same conditions. In vitro, MSF is active at sub-picomolar concentrations in stimulating the production of PF4-like proteins by a rat promegakaryocyte cell line and the synthesis of authentic PF4 in short-term rat bone marrow megakaryocyte cultures.

In the second example, the identical purification procedure, without the Biogel P200 step, is used to isolate nearly homogeneous preparations of MSF from thrombocytopenic plasma. $^{125}$I-MSF from thrombocytopenic plasma behaves identically on SDS-PAGE and analytical TSK G3000 HPLC chromatography to that prepared from HEK cells. However, impurities are present within the plasma derived product, as shown by SDS-PAGE and the three-fold lower specific activity of this material when compared to the HEK derived factor. This is most likely due to the omission of the Biogel P200 gel filtration step which serves to remove low molecular weight contaminants from HEK derived MSF. The Biogel P200 fractionation step was not used during the purification of the stimulatory factor from plasma since the estimate of the specific activity of MSF in thrombocytopenic plasma, approximately sixty-fold lower than in the serum-free HEK supernatants, suggested that the extremely small quantities of active protein would be difficult to recover. The concentration of MSF in thrombocytopenic plasma is calculated to be approximately 0.08 pM.

MSF is specific for megakaryocytes. Preparations of MSF do not exhibit any hemopoietic colony stimulating factor, granulocyte-macrophage-CSF, burst promoting activity, Meg-CSF, nor multi-CSF activities. The stimulatory factor is not active in the 3T3 cell mitogenic assay nor in assays which detect interleukin-1 and interleukin-2. The hemopoietic stimulatory factors which have been purified to date are known to be functional at concentrations comparable to the range noted for this factor. These include Hemopoietin-1 (1.5 pM), GM-CSF (3 pM), and interleukin-3 (5–25 pM). Determinations of the normal serum concentrations of MSF demonstrate that basal levels of this factor fluctuate by about 1.5 to 2.0 fold. The plasma concentrations of MSF appear to be responsive to alterations in the levels of circulating platelets. Results suggest that MSF increases approximately three- to six-fold in the acutely thrombocytopenic animal.

The same initial steps for the purification of TPO from thrombocytopenic plasma, as reported by J. Levin et al. in *Blood* 54, 166a (abstr.) (1979), P. Cohen et al. in *J. Clin. Invest.* 44, 1036 (abstr.) (1965), and E. R. Stanley in *Proc. Natl. Acad. Sci. USA* 82, 2764–2768 (1985), are utilized in the partial purification of MSF from serum-free HEK cell conditioned medium. However, the final MSF product is approximately 1000 fold more pure than the mixtures isolated by Levin et al, Cohen et al and Stanley due to the selection of the conditions for the WGA-Sepharose Chromatography (a linear gradient of N-acetylglucosamine trimers), and the additional steps using a Biogel P200 column (high ionic strength buffer) and a HPLC size exclusion column (low ionic strength buffer).

MSF has been purified and characterized from two sources: serum-free conditioned media obtained from human embryonic kidney cells and thrombocytopenic plasma obtained from New Zealand rabbits. The following materials and methods were used.

Chemicals: Electrophoresis chemicals were purchased from Bio-Rad Laboratories. Na$^{125}$I was purchased from Amersham Radiochemicals Inc. [$^{14}$C] leucine was purchased from New England Nuclear. Lactalbumin hydrolysate was obtained from Gibco. All other chemicals were of reagent grade of better.

Proteins and carbohydrates: Wheat germ agglutinin (WGA), ovomucoid, chitin, N-acetyl glucosamine, bovine serum albumin, ovalbumin, carbonic anhydrase, aprotinin, and other enzymes were purchased from Sigma Chemical Corp. Crude intestinal porcine heparin (121.0 U/mg) was obtained from Diosynth. Chondroitin-4-sulfate and Chondroitin-6-N sulfate were obtained from ICN Biochemicals, Cleveland, Ohio.

Cell lines: RPM cells, as described by Cicoria and Hempling in *J. Cell. Physiol.* 105, 105–127 (1980), were propagated in Dulbecco's Modified Eagle's Medium supplemented with 10% fetal bovine serum. The cells were grown at 37° C. in a humidified atmosphere containing 5% $CO_2$. Penicillin (100 U/ml) and streptomycin (100 microg/ml) were present in all culture media. HEK cells were obtained from M.A. Biologicals and grown in large scale by the M.I.T. Cell Culture Center, Cambridge, MA. The cells were seeded at a density of $6 \times 10^3$ cells/cm in sixty-three 850 cm$^2$ roller bottles and grown to confluency ($5 \times 10^7$ cells/bottle) in a medium containing M199 and 10% fetal bovine serum. After confluency was reached, the cells were maintained in serum-free M199 containing 0.5% lactalbumin hydrolysate, described by T. P. McDonald in *J. Lab Clin. Med.* 85, 59–66 (1975). The supernatants were removed weekly for processing and the serum-free medium replaced for a period of six weeks. Cell counting was performed using a Coulter Counter (Coulter Electronics).

Measurement of protein: Protein concentrations were determining using the Bio-Rad Protein Assay Kit (Coomassie Blue G-250 dye binding), with the exception of the purified material, where the concentration determinations were made by the method of O. H. Lowry et al., *J. Biol. Chem.* 193, 265-275 (1951). Bovine serum albumin was used as the standard in both cases.

Polyacrylamide gel electrophoresis: SDS-PAGE was performed by the procedure of U. K. Laemmli, *Nature* (London) 227, 680-685 (1970). Isoelectric-focusing gel electrophoresis in the presence of 9.2M urea was performed by the method of P. H. O'Farrell, *J. Biol. Chem.* 250, 4007-4021 (1975).

Radioisotopic quantitation: Liquid scintillation counting was performed on a Beckman LS 6800 Scintillation Counter. For autoradiography, Kodak XAR-5 film was exposed at $-70°$ C. and developed according to the manufacturers instructions. Densitometry was performed using a LKB Laser Densitometer. Full scale optical density was set at 1.0.

Chromatographic matrices: Sephadex G-25, Sephadex G-75, DEAE Saphadex A-25 and Sepharose 4B were purchased from Pharmacia Chemicals. Biogel P-200 was obtained from Bio-Rad. TSK-G3000 SW columns were purchased from Toya Soda.

Wheat germ agglutinin (WGA)-Sepharose was prepared by the method of Mintz and Glaser, *Anal. Biochem.*, 97, 423-427 (1979). The binding capacity of the column was 1.1 mg ovomucoid/ml of gel. Heparin-Sepharose was prepared from cetyl-pyridinium chloride precipitated heparin and cyanogen bromide activate Sepharose-4B as described by R. D. Rosenberg et al in *J. Biol. Chem.* 248, 6490-6505 (1973).

Radiolabeling of protein: Radiolabeling of protein with $Na^{125}I$ was performed at $25°$ C. with chloramine-T according to the method of Greenwood and Hunter, *Nature* (London) 194, 495 (1962). Chromatography was conducted at a flow rate of 0.25 ml/minute and fractions of 0.75 ml were collected.

Induction of immune thrombocytopenia and preparation of thrombocytopenic plasma:

Thrombocytopenic plasma was obtained from New Zealand white rabbits (3 kg) that were rendered acutely thrombocytopenic (platelet counts less than 5% of normal) by injection of 3 ml of goat anti-rabbit platelet antisera purchased from East Acres Biologicals, (Southbridge, Mass.) into an ear vein. The antisera injection caused no significant effect on either hematocrit or white cell counts. White blood cell and platelet counts were performed by the procedure of Brecher and Cronkite in *J. Appl. Physiol.* 3, 365-377 (1950). Blood was collected 4 hours after injection via cardiac puncture (approximately 70 ml/rabbit). At this time, the platelet counts had dropped from 500,000/mm$^3$ to 20,000/mm$^3$. The samples were drawn in syringes containing 3.8% sodium citrate (9 parts blood: 1 part citrate solution), and centrifuged at 3,000$\times$g for 20 minutes at 4° C.

Measurement of MSF Activity

MSF activity is assayed as follows using either an RPM cell line or bone marrow depleted of the most mature megakaryocytes by counterflow centrifugal elutriation and Percoll density gradient centrifugation and selectively enriched in the cytoplasmically immature megakaryocytes. The incorporation of [$^{14}$C] leucine into the platelet-specific alpha granule protein, platelet factor 4, as well as the incorporation of $^{35}$S-sulphate into platelet proteoglycans synthesized by the maturing megakaryocytes, are monitored as markers of cytoplasmic maturation. Incorporation of both radiolabels into the specific megakaryocyte synthesized platelet components is increased as much as three-fold in a dose-dependent manner by the purified megakaryocyte stimulatory factor (MSF), without a concomitant increase in general protein synthesis. Rat platelet factor 4 is specifically isolated and characterized by its high affinity for heparin-Sepharose and its amino terminal sequence identity with human and rabbit platelet factor 4. The $^{35}$S-sulfate-labeled proteoglycans are primarily composed of chondroitin 4-sulfate glycosaminoglycans, and are identified as platelet granule components by their secretion by the megakaryocytes in response o thrombin or A23187. Incorporation of the label demonstrates that the purified MSF regulates the synthesis of platelet granule components by megakaryocytes and suggests that this factor may be required to control the rate and/or extract of cytoplasmic development during megakaryocyte maturation.

The rat promegakaryocyte (RPM) cells used in the assay were isolated and cloned from the bone marrow of a Long-Evans rat by Cicoria and Hempling of the University of South Carolina. Previous studies have characterized the RPM cell as a progenitor of the megakaryocyte lineage since it contains several platelet specific markers such as Factor VIII related antigen, fibrinogen, and acetylcholinesterase. These studies have also demonstrated that the RPM cell exhibits other characteristics of the megakaryocyte, such as its ability to take up and release [$^3$H]serotonin via a thrombin inducible mechanism, and its capacity to screte potent mitogenic substances.

The effects of the purified MSF upon the synthesis of platelet alpha granule components in vitro were also tested in isolated rat megakaryocytes. Elutriation and Percoll density gradient centrifugation were used to obtain a population of megakaryocytes, Meg-D, which are cytoplasmically undeveloped as judged by light and electron microscopy. Meg-D exhibit numerous characteristics of immature megakaryocytes including a proportionately large nucleus:cytoplasm volume distribution, relatively few platelet granules, and a poorly-developed surface-connected canalicular system. However, analysis of their extent of ploidization by flow cytometry demonstrates that Meg-D have the same ploidy distribution as Meg-Lt, the most mature population of megakaryocytes isolated by elutriation and Percoll density centrifugation. Meg-D have been observed to mature during short-term in vitro culture with the appearance of granules and the extensive surface-connected open canalicular membrane system as well as by a substantial decrease in the nucleus:cytoplasm volume distribution, indicating that the population has completed the process of polyploidization but has not yet generated a major portion of their final complement of platelet-specific cytoplasmic components.

RPM Assay for MSF Activity

RPM cells are centrifuged, resuspended in leucine-free Minimal Eagle's Medium containing 10% fetal bovine serum and seeded in 24-well cluster plates at a density of $3\times 10^5$/ml (1 ml/well). Two to nine measurements are performed, including the control. Varying amounts of the protein fractions to be assayed, total added volume less than 100 microliters, are added to the wells. Identically fractionated normal plasma is utilized as a control for the ammonium sulfate precipitated material derived from thrombocytopenic plasma. When assaying more purified samples, the fractions are diluted into a protein carrier (0.6 mg/ml ovalbumin) prior to admixture with cells, in order to minimize non-specific adsorption. An equal volume of carrier solution is added to control cultures. Subsequently, 20 microCi of [$^4$C]leucine (340 mCi/mmol) is added to each well, and the plates incubated for 24 hours. The cells in each well are transferred into polypropylene tubes, and centrifuged at 400×g for 5 minutes at 25° C. The cell-free supernatants are removed and discarded. The pelleted cells are resuspended in 1 ml of P$_i$/saline. In order to determine cell numbers within each tube, 200 microl of resuspended cells are diluted into 10 ml of P$_i$/saline and counted in a Coulter Counter. To the 800 microl of suspended cells remaining in each tube, 200 microl of 1.0M NaCl and 50 microl unlabelled PF4-like carrier (0.2 mg/ml, in 1.0M NaCl are added (final [NaCl]=0.4M). The cell suspensions are then cooled to 4° C., sonicated for 30 seconds at 30 watts, and centrifuged at 10,000×g for 5 minutes at 4° C. to remove cell debris. The resulting lysates are applied to 1.0 ml heparin-Sepharose columns equilibrated with 0.01M Tris-HCl, 0.5M NaCl, pH 8.6. The columns are washed with equilibration buffer at a flow rate of 6.0 ml/hour until the radioactive counts eluting from each individual column are less than 150 cpm/50 microliters. The radioactive counts that remain bound to the columns are eluted with a single linear gradient from 0.5M NaCl to 2.0M NaCl in 0.01M Tris-HCl, pH 8.6 (15 ml/reservoir/column), and fractions of 1.25 ml collected.

The radioactive elution profiles of the material that emerges from each heparin-Sepharose column during the 0.5 to 2.0M NaCl gradient demonstrate a single radioactive peak for each column which elutes at a conductivity corresponding to [NaCl]=1.0M. The amount of stimulation is evaluated in two ways: (1) the ratio of the radioactive counts in the 1.0M NaCl peak of the cell samples which were incubated with protein fractions derived from thrombocytopenic plasma vs. the counts in the 1.0M peak of the control sample outlined above, and (2) the ratio of the optical densities of autoradiograms of the PF4-like proteins after SDS-PAGE of stimulated and control cell samples.

In general, the augmentation observed via densitometry is somewhat higher than that observed via radioactive counts, possibly due to the binding on non-PF4-like radiolabeled proteins to the heparin-Sepharose columns. The stimulation is approximately 3.1-fold as determined by the first method, and approximately 5.2-fold as determined by the second technique. The addition of this stimulatory activity to RPM cell cultures has absolutely no effect on the growth rate of the cells (doubling time=24 hours). It also does not alter the incorporation of radioactivity into total protein as determined by the measurement of trichloroacetic acid precipitable counts.

Purified MSF displays a concentration-dependent ability to enhance the synthesis of PF4-like proteins as judged by the RPM cell assay. The maximal stimulation ranges from 4–7-fold, depending on the method of quantitation. The data show that half maximal stimulation occurs at an MSF concentration of 0.0125 ng/ml (0.8 pM), average maximal stimulation is about 3.9-fold, and the maximal extent of stimulation remains relatively constant at MSF concentrations of up to 0.625 ng/ml (41.7 pM). Furthermore, this substance retains full biologic activity for over a year if stored at −80° C.

Dose response curves are determined for the products obtained from each of the steps of the purification procedures. A marked decrease in the stimulatory response occurs for the less purified fractions when their concentrations in the assay are sufficiently high, as shown by a dose response curve determined for the 60–80% ammonium sulfate fraction prepared from thrombocytopenic plasma. The data for the ascending portion of the dose-response curves fit a straight line based on a least squares analysis of the data. A unit of biological activity is therefore defined as the amount of the factor which produces a half-maximal stimulation on the ascending portion of a given dose-response curve.

Isolated Rat Megakaryocyte Assay for MSF Activity

The ability of MSF to stimulate biosynthesis of PF4 is examined using megakaryocytes prepared from Sprague-Dawley-derived (CD) rats (Charles River Breeding Laboratories, Inc., Wilmington, MA) at 1½ to 5 months of age. Bone marrow obtained from 12 ether-anesthetized animals is gently flushed from each tibia and femur into a sterile plastic petri dish with HATCH buffer (a modification of CATCH medium, (*J. Cell Biol.* 69, 159–172 (1976)), calcium and magnesium-free Hank's balanced salt solution containing 1 mM adenosine, 20 mM theophylline, and 0.38% sodium citrate, plus 10 mM HEPES, 0.1% dextrose, 0.5% bovine serum albumin, and 0.15% U/ml apyrase. The marrow is flushed through a 18-gauge needle several times, filtered through 155 micron nylon mesh screens (Spectramesh, Spectrum Medical, Inc., Los Angeles, CA), and diluted to 2 to 5×10$^6$ cells/ml in HATCH buffer for loading into the Sanderson separation chamber of a Beckman elutriator system (Beckman Instruments, Inc., Palo Alto, CA). Prior to use, the system is sterilized with a 70% ethanol solution, rinsed with sterile distilled water, and primed with HATCH buffer. After 2 to 5×10$^8$ marrow cells have been loaded onto the system at a buffer flow rate of 12 to 15 ml/min, at 18° C., and at a rotor speed of 1400 rpm, 80 to 100 ml of HATCH buffer are washed through at 20 to 25 ml/min. The cells washed out of the elutriator chamber at buffer flow rates of 12 to 15 ml/min and 20 to 25 ml/min are called fractions 1 and 2, respectively. At this point, the buffer flow is reversed to remove the megakaryocyte-enriched cell population from the separation chamber through the inlet tubing. The loading and backflushing steps are repeated until all marrow cells had been elutriated. The megakaryocyte-enriched cell suspensions are pooled and collected into sterile plastic centrifuge tubes kept on ice.

The pooled megakaryocyte-enriched cell suspensions are centrifuged at 400×g for 10 minutes at 4° C. and resuspended in a solution of Percoll (Pharmacia Fine Chemical, Piscataway, NJ), diluted with Dulbecco's Modified Eagle's Medium (DMEM) to a final density of 1.050 g/cm$^3$. A discontinuous gradient of three layers is prepared: 10 mls of HATCH buffer, 15 mls of the cell suspension in 1.050 g/cm$^3$ Percoll, and 15 mls of 1.085 g/cm$^3$ Percoll in HATCH buffer. The gradients are centrifuged at 18° C. for 20 minutes at 400×g and the cells collected in three fractions. The lighter megakaryocyte-enriched cell population (Meg-Lt) is collected from the interface between the 1.050 g/cm$^3$ Percoll layer and the overlying buffer layer (density less than 1.050 g/cm³). The more dense megakaryocyte population (Meg-D) consists of the cell layer which forms at the interface between the two Percoll layers, as well as cells in the overlying 1.050 g/cm³ Percoll layer. The pellet fraction consists of the cells in, and below, the 1.085 g/cm³ Percoll layer. Each cell population is diluted four-fold and washed once by centrifugation (400×g, 8 minutes, 4° C.) in HATCH buffer and once in DMEM to remove the Percoll. The cells are counted in a hemocytometer chamber or by using a Coulter Counter (Coulter Electronics).

Cell diameters are determined with a calibrated optical micrometer and megakaryocyte cytoplasmic mass calculated as a proportion of the total cell mass of the culture. Cells of 12.5 microns in diameter or greater can be recognized morphologically as megakaryocytes with certainty and their identity confirmed by staining for acetylcholinesterase activity for 6 hours according to the method of Karnovsky and Roots, *J. Histochem. Cytochem,* 12, 219–221 (1964), as modified by Jackson, *Blood* 42, 413–421 (1973). Quantitation of megakaryocyte acetylcholinesterase activity is performed according to the method of Ellman et al, *Biochem. Pharmac.* 7, 88–95 (1961), as modified by Burstein et al, *J. Cell Physiol.* 122, 159–165 (1985). Cultured or freshly isolated megakaryocyte-enriched suspensions are analyzed for the degree of ploidy by two dimensional flow cytometry as described by Jackson, *Blood,* 63, 768–778 (1984).

The isolated megakaryocytes are suspended in Dulbecco's Modified Eagle's Medium (DMEM) supplemented with 10 mM HEPES, or Iscove's Modified Dulbecco's Medium (IMDM), containing 10% (vol/vol) horse serum (Grand Island Biological Co., Grand Island, NY). The suspensions of megakaryocytes are cultured in 24-well cluster plates (Costar, Cambridge, MA) in 1.5 ml culture medium with 5% $CO_2$ at 37° C. for periods up to 3 days.

For labeling of megakaryocyte proteins, cells are incubated for the last 24 hours of culture in the presence of 40 microC/ml [$^{14}$C]-leucine (New England Nuclear, Boston, MA) in leucine-free DMEM or IMDM containing 10% horse serum, MSF, plus 10% medium conditioned by culture of the megakaryocytes prior to the labeling period. In order to label megakaryocyte proteoglycans, carrier-free $^{35}SO_4$ is added to the cultures in sulfate-free DMEM or IMDM containing horse serum, MSF, and conditioned medium.

After culture, ten millimolar EDTA, 100 U/ml aprotinin, and 10 microg/ml soybean trypsin inhibitor are added, the isolated megakaryocyte cells centrifuged at 400×g for 10 minutes, and resuspended in 100 microliters HATCH buffer. Cold carrier protein (50 microg) prepared from unlabeled rat platelet PF4 is added, the cells lysed in 1.5M NaCl (by the addition of an equal volume of 3M NaCl), sonicated, and centrifuged at 10,000×g for 3 minutes to remove cellular debris. Aliquots are precipitated with trichloroacetic acid, neutralized with 1N NaOH and counted on a Beckman LS 6800 Scintillation Counter using Ultrafluor scintillation fluid (National Diagnostics, Somerville, NJ). The remaining high-salt lysed cell suspensions are diluted to 0.15M NaCl and purified by heparin-Sepharose affinity chromatography. The quantitation of radiolabeled PF4 on the heparin-Sepharose column is then used to determine the rate of synthesis of PF4 as a function of MSF in short-term cultures of megakaryocytes.

Structural studies show that rat PF4 is quite homologous with human and rabbit PF4, respectively. The major molecular species of radiolabeled megakaryocyte PF4 isolated by heparin-Sepharose chromatography exhibits size and charge characteristics identical to rat PF4 as judged by two-dimensional electrophoresis and possesses immunochemical epitopes similar to rat PF4 as judged by immunoblot analysis and precipitation with antibodies directed against the latter alpha granule protein. The predominant rat platelet PF4 molecule has an $M_r$ of approximately 9670 by amino acid analysis and SDS-PAGE. However, a 19,000 dalton molecular weight form is often present in varying amounts and probably represents a non-dissociable dimer of the lower molecule weight species.

Antisera to PF4 for use in immunochemical analysis is prepared from rabbits innoculated initially with a 1:1 mixture of 50 to 100 microg of rat PF4 or in complete Freund's adjuvant (Grand Island Biological Company, Grand Island, NY), and subsequently in incomplete Freund's adjuvant at weekly intervals. Rabbits are bled from the ear vein periodically to monitor the level of antibodies produced. When unfractionated antisera is used in immunoblot analysis of whole platelet lysates, only two bands are visualized with the same molecular weights as the purified rat PF4. Both species of the purified rat PF4 are recognized by antibodies prepared against either of the molecular weight species and affinity fractionated on PF4-conjugated Sepharose 2B.

Comparison of autoradiograms and immunoblotted chromatograms of the material secreted by thrombin activation with the material remaining in the megakaryocyte cell pellet reveals large molecular weight proteins in the pellet which may be precursor forms not yet packaged for secretion in the megakaryocyte alpha granule. Non-immunoreactive proteins are also present in small amounts and are undoubtedly due to minor contaminants. The levels of rat PF4 produced by megakaryocytes are determined by isolating [$^{14}$C]-labeled components from these polyploid cells via heparin-Sepharose chromatography and quantitating the amounts of radiolabel present within the appropriate regions of the SDS-PAGE autoradiograms by densitometric scans.

MSF stimulates the synthesis of rat PF4 by cultured, polyploid megakaryocytes in a dose-dependent fashion without altering the extent of general protein synthesis or cell viability within the cultures. The maximal stimulatory effect upon PF4 synthesis is about three-fold in response to 0.625 ng/ml of MSF.

Human PF4 is packaged in platelet alpha granules with a chonroitin sulfate proteoglycan carrier in a stoichiometric complex consisting of 8 moles of PF4 and 2 moles of proteoglycan. Rat megakaryocytes take up $^{35}$S-sulfate rapidly under in vivo, as well as in vitro conditions, and incorporate it into membrane and alpha granule components. Chondroitin sulfate has been identified as the major sulfated glycosaminoglycan in rat platelets. MSF stimulates the production of the chondroitin sulfate carrier, as well as rat PF4. Meg-D and Meg-Lt were cultured in the presence of $^{35}SO_4$, cells and culture media were extensively proteolyzed, and DEAE Sephadex chromatography was utilized to isolate the glycosaminoglycans. The final product is predominantly chondroitin 4-sulfate. As much as 70% of the radiolabeled chondroitin 4-sulfate is specifically released from cultured megakaryocytes by platelet agonists which indicates that the glycosaminoglycans are present within granules. These tests repeated in the presence of various concentrations of MSF reveal that chondroitin 4-sulfate synthesis is stimulated by the above factor in a dose-dependent fashion with as little as 0.625 ng/ml of MSF sufficient to augment the production of the glycosaminoglycan by about three-fold.

Based upon these results, MSF is able either to enhance the synthesis of increasing numbers of chondroitin 4-sulfate chains per proteoglycan core or, more likely, augment the production of increasing numbers of chondroitin 4-sulfate proteoglycans within the alpha granules of maturing rat megakaryocytes.

Purified MSF has also been assayed in a plasma clot system designed to measure colony stimulating factor (CSF) activities. Blast-forming unit-CSF, granulocyte-macrophage-CSF, or megakaryocyte-CSF activties are not detected when 0.025 ng/ml to 25 ng/ml of the stimulatory factor is added to the assay system. Furthermore, MSF is not active in the 3T3 mitogenic assay and pure gamma-interferon is not potent in the MSF assay.

buffer. Chromatography is conducted at a flow-rate of 6 ml/hr and 4 ml fractions are collected. The appropriate fractions are pooled and concentrated in dialysis bags which are placed in contact with dry Sephadex G-75. The concentrate from the P200 step (5.0 mg, 0.7 mg/ml), is dialyzed vs. buffer A and chromatographed on a TSK-G3000 HPLC size-exclusion column (7.5 mm×60 cm) at 25° C. Multiple 300 ml injections are performed. The columns are equilibrated with 5 mM Tris-HCl, pH 7.2, low ionic strength buffer, at a flow rate of 1.0 ml/min.

The purification data for a purification of MSF using ammonium sulfate precipitation, WGA-Sepharose affinity chromatography, Biogel P200 gel-filtration, and TSK G3000 HPLC gel filtration chromatography are summarized in Table 1. These data represent an average of three separate fractionations.

TABLE 1

| | Purification OF MSF from HEK Cells | | | | |
|---|---|---|---|---|---|
| STEP | AMOUNT OF PROTEIN (MG) | TOTAL ACTIVITY (UNITS) | SPECIFIC ACTIVITY (UNITS/MG) | TOTAL % RECOVERY | TOTAL PURIFICATION FACTOR |
| HEK supernatant | 50,000.00 | $1.0 \times 10^6$ | 20 | — | 1 |
| $(NH_4)_2SO_4$ precipitate | 5,696.00 | $1.7 \times 10^6$ | 300 | 100 | 15 |
| WGA-Sepharose | 25.30 | $10.2 \times 10^5$ | $4.0 \times 10^4$ | 60 | $2.0 \times 10^3$ |
| Biogel P200 | 5.00 | $9.0 \times 10^5$ | $1.6 \times 10^4$ | 56 | $8.0 \times 10^3$ |
| TSK-G3000 SW | 0.23 | $3.5 \times 10^6$ | $1.5 \times 10^7$ | 209 | $7.5 \times 10^5$ |

Purification of MSF Protein from HEK cell supernatants

All steps of the purification procedure are performed at 4° C., unless otherwise noted. The serum free supernatants (15 liters/week, 0.5 mg/ml), are concentrated 300-fold using a Pellicon cassette ultrafiltration system (Millipore), precipitated with ammonium sulfate at 80% saturation, centrifuged at 15,000×g for 20 minutes, and stored at −70° C. After a six week accumulation, the pellets are resuspended in 120 ml of a buffer containing 0.05M Tris-HCl, 0.15M NaCl, pH 7.4 (buffer A) and 1 mM phenylmethylsulfonylfluoride, and dialyzed vs. 3 changes of 4 L of buffer A. After dialysis, insoluble material, which accounts for as much as 90% of the initial protein, is removed by centrifugation at 5000×g for 10 min at 4° C.

The material obtained from the ammonium sulfate step (5,696 mg, 400 ml) is divided into aliquots. Each aliquot is applied to 25 ml WGA-Sepharose columns equilibrated with buffer A. The columns, operated at a flow rate of 10 ml/min, are washed with equilibration buffer until $A_{280}$ is less than 0.02, and then eluted with chitin oligosaccharides, preferably N-acetylglucosamine trimers, at a concentration of 12 mM (reducing end concentration, average number of saccharide units/reducing end=2.5) in buffer A. The active protein eluted from the WGA-Sepharose step (25.5 mg, 0.3 mg/ml) is concentrated under pressure using a YM5 ultrafiltration membrane (Amicon).

The final volume, approximately 8 ml, is divided into 2.0 ml aliquots, each of which is applied to a Biogel P200 column (120 cm×1.4 cm diam., 185 ml), equilibrated in buffer A, a relatively high ionic strength Briefly, the ammonium sulfate precipitation and subsequent dialysis provide a 8.2-fold purification with a complete recovery of activity. The WGA-Sepharose step provides a 70-fold purification, with recovery of 60% of the applied activity. 90% of the stimulatory activity elutes from the Biogel P200 column at the leading edge of the void volume. This step yields a 4-fold purification and an 88% recovery of applied activity. Most significantly, filtration on Biogel P200 removes low molecular-weight contaminants that would have been difficult to resolve from the final product during the subsequent TSK G3000 chromatography. The bulk of recoverable activity (greater than 90%) elutes as a sharp peak of protein with an Mr=9,000, and a specific activity=$1.4 \times 10^7$ units/mg from a TSK G300 SW column. Based on the specific activity of the final product, the total purification factor achieved using this procedure is $7.5 \times 10^5$.

Purification from Thrombocytopenic Plasma

Thrombocytopenic plasma (300 ml) is prepared from rabbits that have been rendered actutely thrombocytopenic by antiplatelet antisera injection, as described above. The specific activity of this starting material is 0.33 units/mg. The combination of ammonium sulfate fractionation, WGA-Sepharose chromatography, and TSK gel filtration chromatography allows MSF to be purified about $1.44 \times 10^7$ fold from thrombocytopenic plasma with an overall recovery of applied activity of about 45%. Greater than 90% of the biologic activity is detected in the region of the $A_{270}$ profile from the TSK-3000 column corresponding to protein with an $M_r$=9,000. Approximately 0.4 microgram of protein with a specific activity of $4.8 \times 10^6$ units/mg is recovered. This specific activity is 3-fold lower than that obtained from HEK cell supernatants.

In the present invention, physically homogeneous preparations of megakaryocyte stimulatory factor (MSF) isolated from the production medium of human embryonic kidney cells or from thrombocytopenic serum show that picomolar concentrations of MSF are able to stimulate the synthesis of platelet factor 4 and the chondroitin sulfate carrier which are found in the platelet and megakaryocyte alpha-granules. On this basis, it is hypothesized that MSF is critically involved in regulating the functional capacity of circulating platelets by its effect on the synthesis of platelet-specific granule components within cytoplasmically immature megakaryocytes in the bone marrow. Multiple practical applications for the purified factor follow, including treatment of thrombocytopenic patients, patients with decreased wound healing, and in the development of drugs and antibodies for use in regulating the in vivo MSF activity.

The nucleotide sequences, either the DNA or cDNA, encoding the MSF can be isolated by methods known to those skilled in the art. The gene is more difficult to isolate than many because it is devoid of methionine and the N-terminal region is blocked.

The preferred method to isolate the gene or other nucleotide sequences encoding MSF is as follows: Total RNA is prepared from $5 \times 10^7$ HEK cells which are producing MSF, as judged by the previously described assays, by guanidine-HCl extraction. Polyadenylated RNA is then isolated by two cycles of chromatography on oligo(dT) cellulose. First strand cDNAs are synthesized with reverse transcriptase using oligo(dT) as a primer, and second strand cDNA is generated with *E. coli* DNA Polymerase and Ribonuclease H according to the method of Okayama and Berg, *Mol. Cell Biol.* 2, 161–170 (1982), as modified by Gubler and Hoffman, *Gene* 25: 263–269 (1983), except that Actinomycin D is employed in the final reaction mixture at a concentration of 50 mg/ml. T4 DNA Polymerase is utilized to produce blunt ends. Repaired cDNAs are coupled to synthetic EcoRI linkers after protection of internal sites with EcoRI methylase. The linker ligated cDNAs are digested with EcoRI and separated from free linkers using Sepharose CL 4B chromatography. This material is then ligated to the EcoRI digested alkaline phosphatase treated phage expression vector, 1GT 11, packaged in vitro, and plated on *E. coli* host strain Y1088 (*Gene* 25, 263–269, (1983); *DNA cloning techniques: A practical approach*, eds. D. Glover (IRL Press, Oxford, 1984); *Science* 222, 778–782 (1983)).

A rabbit anti-rat MSF IgG heteroantibody can be utilized to detect bacterial clones possessing fusion proteins of MSF. To this end, recombinant clones can be screened as phage plaques on *E. coli* host strain Y1090 according to the technique of Young and Davis, *Science*, 222, 778–782 (1983). The detected candidate plaques can then be taken through several rounds of plaque purification and immunochemical screening. The fusion proteins can be further characterized by preparing lysogens of 1GT-MSF and non-recombinant 1GT11 in *E. coli* host strain Y1089, as outlined by Young and Davis, *Proc. Natl. Acad. Sci. USA* 80: 1194–1198 (1983). The phage is induced by shifting the temperature to 45° C. to inactivate the repressor and the production of b-galactosidase or fusion protein initiated with IPTG at a final concentration of 5 mM. Cell lysates are precipitated at 4° C. with 33% (vol/vol) saturated ammonium sulfate, and then examined by SDS-PAGE, as well as Western blot analyses, utilizing affinity fractionated anti-rat MSF IgG heteroantibody followed by Gold-labelled anti-rabbit IgG as outlined in the manufacturer's instructions.

The isolated DNA from the recombinant phage can be subjected to EcoRI digestion to obtain insert fragments, subcloned into M13mp8, and sequenced by the dideoxy chain termination method of Biggin et al., *Proc. Natl. Acad. Sci. USA* 80, 2963–3965 (1983). If necessary, the inserts can be used to rescreen the cDNA library by the technique of Benton and Davis, *Proc. Natl. Acad. Sci. USA* 80, 1194–1198 (1983), in order to obtain full length clones.

Confirmation of the structure of MSF will be sought by cleaving the protein with proteolytic enzymes such as trypsin, separating the resultant polypeptides by reverse phase HPLC, and determining the amino acid sequence of the components by vapor phase sequencing. In the unlikely event that heteroantibody probes are not able to identify clones with MSF inserts, the amino acid sequence data obtained from MSF will be employed to design appropriate oligonucleotides so that these probes can be utilized to obtain the initial recombinants with inserts from MSF. The approach to isolating full length clones will thereafter be identical to the method outlined above.

These nucleotide sequences may be used to produce MSF in genetically engineered organisms. The gene may also be modified to produce MSF with altered activity.

Although this invention has been described with reference to its preferred embodiments, other variations and modifications will be apparent to those skilled in the art and it is intended to include all such variations and modifications within the scope of the appended claims.

I claim:

1. A method for isolating a megakaryocyte stimulatory factor comprising:
    a. preparing a concentrated serum-free supernatant from the cell culture medium of HEK cells;
    b. contacting said supernatant with ammonium sulfate having greater than 50% saturation, under conditions sufficient to cause precipitation of proteins in the supernatant;
    c. contacting the precipitated proteins obtained in step (b) with buffer comprising Tris-HCl and NaCl under conditions sufficient to solubilize the protein containing the megakaryocyte stimulatory factor;
    d. contacting the soluble fraction obtained in step (c) with a lectin-Sepharose resin under conditions sufficient to cause the protein containing the megakaryocyte stimulatory factor to bind to the resin;
    e. contacting the lectin-Sepharose resin with chitin oligosaccharides under conditions sufficient to elute the megakaryocyte stimulatory factor from the resin;
    f. contacting the eluant from step (e) with a first size-exclusion gel and collecting the fractions obtained therefrom;
    g. contacting the fractions obtained in step (f) with a second size-exclusion gel, and collecting the purified megakaryocyte stimulatory factor therefrom.

2. A method of claim 1, wherein the ammonium sulfate solution is 80% saturated.

3. A method of claim 1, wherein the lectin-sepharose resin is WGA-sepharose resin.

4. A method of claim 1, wherein the chitin oligosaccharides are N-acetyl glucosamine trimers.

5. A method of claim 4, wherein the concentration of N-acetyl glucosamine trimers is about 12 mM.

6. A method of claim 1, wherein said first size-exclusion gel has a molecular weight exclusion of about 200 KD.

7. A method of claim 6, wherein said size exclusion gel is Biogel P200.

8. A method of claim 7, wherein the fractions are eluted from the gel with a high ionic strength buffer.

9. A method of claim 1, wherein the second size exclusion gel is TSK G3000.

10. A method of claim 9, wherein the fractions are eluted from the second resin with a low ionic strength buffer.

11. A method of claim 1, wherein thrombocytopenic plasma is provided in place of the supernatant from the cell culture medium of HEK cells, and wherein step (f) is omitted.

12. A method for isolating a megakaryocyte stimulatory factory comprising:
   a. preparing a concentrated serum-free supernatant from the cell culture medium of HEK cells;
   b. contacting said supernatant with ammonium sulfate having 80% saturation, under conditions sufficient to cause precipitation of proteins in the supernatant;
   c. contacting the precipitated proteins obtained in step (b) with buffer comprising Tris-HCl and NaCl (pH 7.4) under conditions sufficient to solubilize the protein containing the megakaryocyte stimulatory factor;
   d. contacting the soluble fraction obtained in step (c) with a WGA Sepharose resin under conditions sufficient to cause the protein containing the megakaryocyte stimulating factor to bind to the resin;
   e. contacting the WGA-Sepharose resin with a solution containing N-acetyl glucosamine trimers under conditions sufficient to elute the megakaryocyte stimulatory factor from the resin;
   f. contacting the eluant from step (e) with a Biogel P200 gel and collecting the fractions obtained therefrom;
   g. contacting the fractions obtained in step (f) with a TSK G3000 gel, and collecting the purified megakaryocyte stimulatory factor therefrom.

13. A method for isolating a megakaryocyte stimulatory factor comprising;
   a. preparing a thrombocytopenic plasma;
   b. contacting said plasma with ammonium sulfate having 80% saturation, under conditions sufficient to cause precipitation of proteins in the plasma;
   c. contacting the precipitated proteins obtained in step (b) with buffer comprising Tris-HCl and NaCl (pH 7.4) under conditions sufficient to solubilize the protein containing the megakaryocyte stimulatory factor;
   d. contacting the soluble fraction obtained in step (c) with a WGA-Sepharose resin under conditions sufficient to cause the protein containing the megakaryocyte stimulatory factor to bind to the resin;
   e. contacting the WGA-Sepharose resin with N-acetyl glucosamune trimers under conditions sufficient to elute the megakaryocyte stimulatory factor from the resin;
   f. contacting the eluant from step (e) with a TSK G3000 gel, and collecting the purified megakaryocyte stimulatory factor therefrom.

* * * * *